United States Patent
Ropars et al.

(10) Patent No.: US 9,453,245 B2
(45) Date of Patent: Sep. 27, 2016

(54) METHOD FOR PRODUCING ETHANOL AND SOLVENTS FROM LIGNOCELLULOSIC BIOMASS INCLUDING THE RECIRCULATION OF A BUTYL WINE OBTAINED BY FERMENTING PENTOSES

(75) Inventors: Marcel Ropars, Palaiseau (FR); Caroline Aymard, Lyons (FR); Rejane Dastillung, Lyons (FR); Remy Marchal, Chatou (FR); Sandra Menir, Gonesse (FR); Benjamin Clement, Saint Maur Des Fosses (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 40 days.

(21) Appl. No.: 14/110,713

(22) PCT Filed: Apr. 4, 2012

(86) PCT No.: PCT/FR2012/000125
§ 371 (c)(1),
(2), (4) Date: Oct. 28, 2013

(87) PCT Pub. No.: WO2012/140334
PCT Pub. Date: Oct. 18, 2012

(65) Prior Publication Data
US 2014/0065683 A1 Mar. 6, 2014

(30) Foreign Application Priority Data
Apr. 14, 2011 (FR) ...................... 11/01148

(51) Int. Cl.
| | |
|---|---|
| C12P 7/16 | (2006.01) |
| C12P 7/10 | (2006.01) |
| C12P 7/14 | (2006.01) |
| C12P 7/28 | (2006.01) |

(52) U.S. Cl.
CPC .. *C12P 7/16* (2013.01); *C12P 7/10* (2013.01); *C12P 7/14* (2013.01); *C12P 7/28* (2013.01); *Y02E 50/10* (2013.01); *Y02E 50/16* (2013.01)

(58) Field of Classification Search
None
See application file for complete search history.

(56) References Cited

U.S. PATENT DOCUMENTS

| | | |
|---|---|---|
| 8,123,864 B2 | 2/2012 | Christensen et al. |
| 8,367,378 B2 | 2/2013 | Balan et al. |
| 8,460,473 B2 | 6/2013 | Christensen et al. |
| 2009/0093027 A1 | 4/2009 | Balan et al. |
| 2010/0041119 A1 | 2/2010 | Christensen et al. |
| 2012/0100585 A1 | 4/2012 | Ropars et al. |
| 2012/0138246 A1 | 6/2012 | Christensen et al. |
| 2013/0143263 A1 | 6/2013 | Christensen et al. |

FOREIGN PATENT DOCUMENTS

| | | |
|---|---|---|
| WO | 2007009463 A2 | 1/2007 |
| WO | 2010130888 A2 | 11/2010 |

OTHER PUBLICATIONS

International Search from PCT/FR2012/000125 dated Aug. 30, 2012.
Jae-Hyung Ahn et al. "Butanol production from thin stillage using *Clostridium pasteurianum*" Bioresource Technology, vol. 102, [2011], pp. 4934-4937.
Abhijit Dutta, et al. "An Economic Comparison of Different Fermentation Configurations to Convert Corn Stover to Ethanol Using *Z. mobilis* and Saccharomyces" Biotechnology Progress, vol. 26, No. 1, [2010], pp. 64-72.
Carlo N. Hamelinck et al. Ethanol from lignocellulosic biomass: techno-economic performance in short-, middle-and long-term Biomass and Bioenergy, vol. 28, No. 4, [2005], pp. 384-410.
Manish Kumar et al. "Developments in biobutanol production: New insights" Applied Energy, vol. 88, No. 6, [2011], pp. 1999-2012.
Nasib Qureshi et al. "Production of butanol (a biofuel) from agricultural residues: Part I-Use of barley straw hydrolysate" Biomass and Bioenergy, vol. 34, No. 4, [2010], pp. 559-565.

*Primary Examiner* — Paul Holland
(74) *Attorney, Agent, or Firm* — Millen, White, Zelano & Branigan, P.C.

(57) ABSTRACT

This invention describes a process for the production of second generation alcohols and/or solvents starting from cellulosic or lignocellulosic biomass wherein the lignocellulosic or cellulosic biomass undergoes a pretreatment before being converted into ethanol after an enzymatic hydrolysis and an ethylic fermentation, wherein glucidic polymers of the pretreated plant are hydrolyzed by cellulases; microorganisms that primarily use hexoses and preferably glucose and mannose are used for the ethylic fermentation; wines, with or without separation of materials in suspension are extracted by distillation; pentoses in the vinasses are fermented by a solventogenic microorganism into a butyl wine, and at least one portion of the butyl wine is recycled upstream from enzymatic hydrolysis.

8 Claims, 2 Drawing Sheets

METHOD FOR PRODUCING ETHANOL AND SOLVENTS FROM LIGNOCELLULOSIC BIOMASS INCLUDING THE RECIRCULATION OF A BUTYL WINE OBTAINED BY FERMENTING PENTOSES

FIELD OF THE INVENTION

This invention is part of the framework of a process for the production of so-called "second-generation" alcohols and/or solvents starting from lignocellulosic biomass. It relates more particularly to a process for the production of ethanol and/or solvents.

PRIOR ART

The lignocellulosic biomass represents one of the most abundant renewable resources on earth. The substrates under consideration are highly variable, since they relate simultaneously to the ligneous substrates (leafy and resinous), the sub-products of agriculture (straw), or those of the industries that generate lignocellulosic waste (farm produce and paper-making industries).

The lignocellulosic biomass consists of three main polymers: cellulose (35 to 50%), hemicellulose (20 to 30%), which is a polysaccharide that consists essentially of pentoses and hexoses, and lignin (15 to 25%), which is a polymer of complex structure and of high molecular weight, composed of aromatic alcohols connected by ether bonds.

These different molecules are responsible for the inherent properties of the plant wall and are organized in a complex intergrowth.

Cellulose and optionally hemicelluloses are the targets of enzymatic hydrolysis but they are not directly accessible to enzymes. This is the reason for which these substrates should undergo a pretreatment preceding the enzymatic hydrolysis stage. The object of the pretreatment is to modify the physical and physico-chemical properties of the lignocellulosic material for the purpose of improving the accessibility of the cellulose that is imprisoned within the lignin and hemicellulose matrix.

Numerous technologies for implementing this pretreatment exist: acid baking, alkaline baking, vapor explosion, organosolv methods, etc. The effectiveness of pretreatment is measured both by the material balance at the end of the pretreatment (recovery level of sugars in soluble monomer or oligomer form or in insoluble polymer form) and also by the cellulosic and hemicellulosic residues' susceptibility to enzymatic hydrolysis.

The processes for the production of alcohols and/or solvents starting from lignocellulosic biomass, so-called "second-generation processes," comprise at least the following stages:

Pretreatment of the substrate,
Enzymatic hydrolysis of the pretreated substrate,
Fermentation of the hydrolyzate that is obtained, and
Separation/purification of the alcohol and/or solvents obtained after fermentation.

The economic validity of this type of process for the production of alcohol and/or solvents is difficult to achieve even for the operators that have broad mobilizable resources. Several items have a strong impact on overall expense including plant resources and energy for the extraction that is most often implemented by distillation. The optimization of this type of process necessarily passes through optimum upgrading of all of the sugars, and in particular the pentoses obtained from hydrolysis by the best-suited microorganisms.

The *Saccharomyces cerevisiae* yeast is the best-performing organism for the production of ethanol, but, without genetic modifications, it uses only hexoses (glucose, mannose, and, to a lesser degree, galactose).

The upgrading of pentoses into ethanol has always constituted a major problem for the process in its entirety. If certain wild yeasts are capable of converting these pentoses into ethanol, they necessarily have to be cultivated in microaerobiosis for having satisfactory performances.

The wild alcohologenic yeasts such as *Saccharomyces cerevisiae* are known for being the most effective microorganisms for the conversion of hexoses into ethanol. These wild yeasts are not capable of converting pentoses without a genetic modification. The use of genetically modified microorganisms complicates the management of the installations and that of the process. Thus, the modified yeasts will always use hexoses on a priority basis, and they can then use these pentoses only in the presence of a limited quantity of glucose that it is suitable to provide by a continuous supply to the microorganism. It is actually known that the rate of consumption of the pentoses is considerably less than that of hexoses (Hahn-Hägerdal et al., Appl Microbiol Biotechno 2007 74: 937-953).

In contrast, the extraction of alcohols and/or solvents implemented by distillation is a particularly energy-intensive item. For the improvement of the economic balance sheet of the production of ethanol and/or solvents, it is suitable to consider reducing the volumes of water, in particular by means of recycling and/or combining different streams that concentrate the solvents.

The patent application WO 2009/065504 has a process for the production of alcohols and in particular butanol in which the vinasses from distillation also containing an acetone-butanol-ethanol mixture are recycled for optimizing the operation of the distillation column. The extraction costs are reduced, and the fermentation productivity is improved.

One of the ways to upgrade pentoses is to convert them into butanol by the bacteria of the genus *Clostridium*, for example, under strictly anaerobic conditions. These microorganisms generally produce other alcohols and/or solvents during the synthesis of butanol, such as, for example, acetone, ethanol or isopropanol. Isopropanol is also produced, often instead of acetone, and mention is then made of the IBE mixture. The butanol, majority component, offers the advantage of having a net calorific value (or PCI) that is higher than that of ethanol.

This invention describes a process for the production of alcohols and/or solvents in which a portion of the butyl wine, produced primarily from pentoses, is recycled within the line for conversion of hexoses into ethanol for reducing the overall cost of the extraction and for benefiting from the bacteriostatic effect of butanol.

SUMMARY OF THE INVENTION

This invention relates to a process for the production of so-called second-generation alcohols and/or solvents, in which the lignocellulosic or cellulosic biomass undergoes a pretreatment before being converted into ethanol after an enzymatic hydrolysis and an ethylic fermentation. The glucidic polymers of the pretreated plant are hydrolyzed by cellulases. Microorganisms that are used for the ethylic fermentation primarily use hexoses and preferably glucose and mannose. Wines, with or without separation of materials in suspension (MES), are extracted by distillation. The vinasses primarily contain the pentoses that have not been used. These pentoses are fermented by a solventogenic microorganism into a butyl wine, and at least one portion of the butyl wine is recycled upstream from enzymatic hydrolysis. The enzymatic hydrolysis and the ethylic fermentation are therefore implemented, separately or simultaneously, in the presence of a portion of butyl wine, a mixture that does not hamper the performance of the enzymes and the yeast under the prevailing conditions.

DETAILED DESCRIPTION OF THE INVENTION

Figure 1:
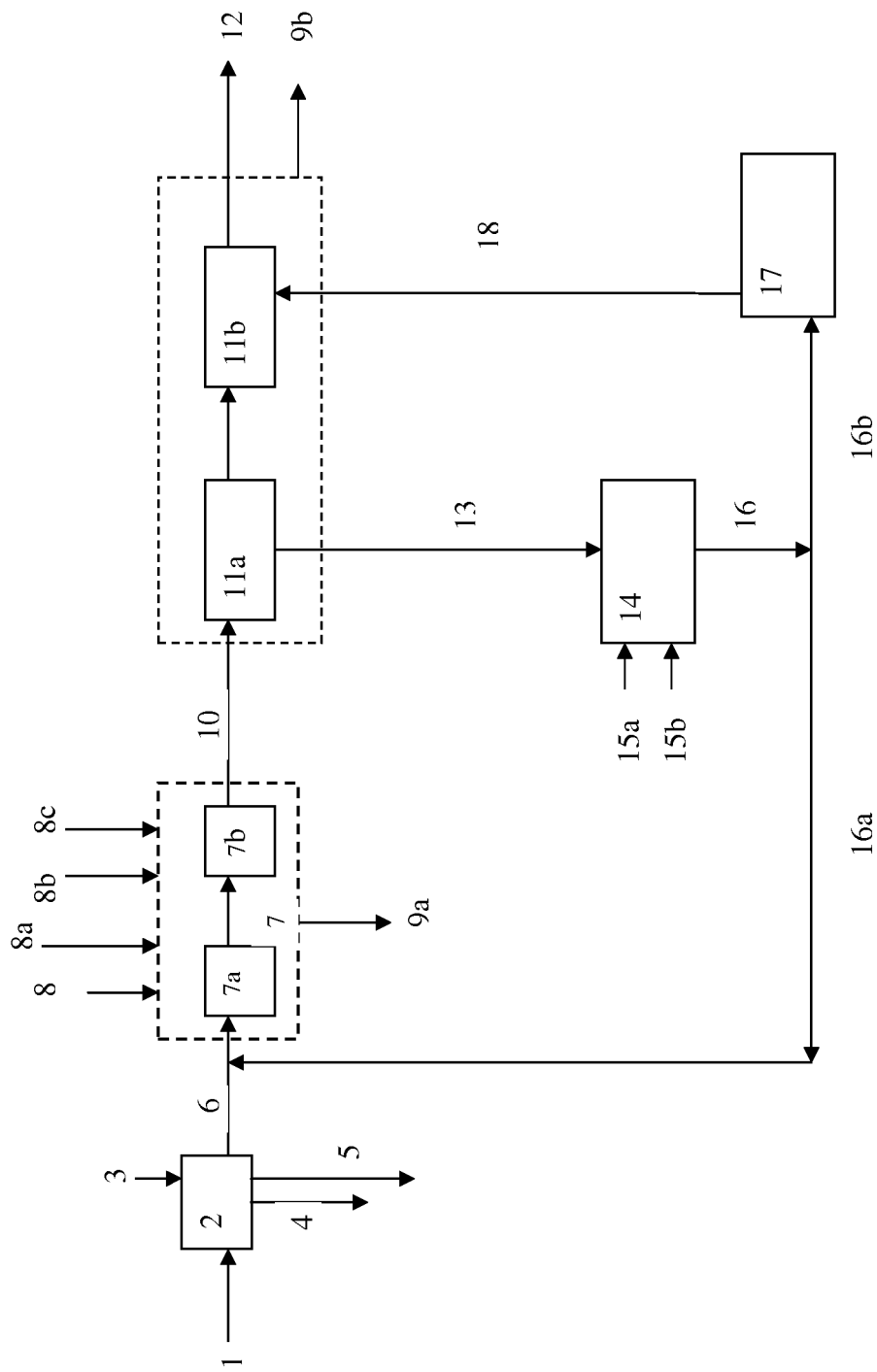
FIG. 1 is a diagrammatic representation of a process for the production of alcohols and/or solvents starting from lignocellulosic substrates, comprising a stage for recycling butyl wine, according to a first embodiment.

This invention describes a process for the production of alcohols and/or solvents starting from cellulosic or lignocellulosic biomass that comprises at least
  a) One stage for thermochemical pretreatment of a cellulosic or lignocellulosic substrate;
  b) Optionally one stage for washing the pretreated substrate and setting the pH;
  c) One stage for enzymatic hydrolysis of the substrate that is pretreated and optionally washed, using cellulolytic and/or hemicellulolytic enzymes producing a hydrolyzate and a water-insoluble residue;
  d) One stage for ethylic fermentation of the hexoses contained in the hydrolyzate obtained from stage c) into ethanol by an alcohologenic microorganism and production of an ethyl wine;
  e) One stage for extraction comprising
    e1) The separation and purification of alcohol and/or solvents obtained from stage d), and
    e2) The separation of a solid cake that contains the insoluble residue and production of vinasses;
  f) One stage for butylic fermentation of pentoses contained in the vinasses obtained in stage e2) by a solventogenic microorganism and production of a butyl wine;
in which at least a portion of the butyl wine is recycled upstream from at least one of the stages of enzymatic hydrolysis and/or ethylic fermentation.

In terms of this invention, the soluble monomers and oligomers of sugars comprising 5 carbon atoms are referred to by the term "pentoses," and the soluble monomers and oligomers of sugars comprising 6 carbon atoms are referred to by the term "hexoses."

The dry materials (solid and soluble) present in one medium are referred to by the abbreviation MS, and the materials in suspension (solids) present in one medium are referred to by the abbreviation MES.

The butylic fermentation generally leads to the production of co-products, called upgradable solvents, below, whose composition and amount depend on the solventogenic microorganism that is used. For example, the acetonobutylic fermentation, also called ABE fermentation, produces a mixture of solvents comprising acetone, butanol, and ethanol. The IBE fermentation produces a mixture of solvents comprising isopropanol, butanol and ethanol.

The wine containing at least the ethanol that is obtained in stage d) of the process according to the invention is called ethyl wine by differentiation from the wine that is obtained at the end of the butylic fermentation stage, which is called "butyl" wine.

Thus, owing to the process according to this invention, it is possible to improve the energy balance of the extraction stage considerably. Actually, with the butyl and ethyl wines being grouped, a single extraction stage is necessary. The savings is approximately 5% to 50%.

The process according to the invention makes it possible in addition to use microorganisms, either alcohologenic, which lead to the formation of ethanol, or solventogenic, which lead to the formation of butanol under optimized conditions for each of them.

Under these conditions, the production of butanol contributes to an advantageous upgrading of pentoses, particularly because of a high PCI for the butanol, thus making it advantageous in the formulation of fuels, and, in contrast, because it contributes to a good miscibility of alcohols within the hydrocarbon phase.

The other products, such as acetone or isopropanol, whose distributions depend on the strain used, are also upgradable in the field of fuels or green chemistry.

In contrast, the process according to this invention makes it possible to benefit from the toxicity of butanol for an anti-bacterial protection in ethylic fermentation. Actually, the butanol is a particularly toxic solvent for numerous microorganisms and in particular for *Clostridium* itself, which cannot support a concentration of greater than 13-15 g/L of butanol since it disrupts the bacterial walls. The *Saccharomyces cerevisiae* yeast that withstands ethanol concentrations that can reach 130 g/L (Alfenore et al., Appl. Microbiol. Biotechnol, 63, 537-542, 2004) is capable of withstanding concentrations of greater than 10 g/L of butanol, which significantly limits the bacterial contaminations that develop both at 35 and at 50° C. This is particularly advantageous in the case of alkaline pretreatment because the absence of inhibiting compounds obtained from the degradation of lignin makes the medium particularly sensitive to contaminations.

The cellulosic or lignocellulosic substrate used in the process according to this invention is selected from among the most varied biomasses, but more particularly from the resinous arborescent types (softwood such as spruce or pine) or leafy arborescent types (hardwood such as eucalyptus) or else agricultural lignocellulosic waste (straw from corn, rice, etc.), or else dedicated cultures (Miscanthus, switchgrass).

Prior to the thermochemical pretreatment, the biomass can undergo a mechanical treatment, for example of the grinding type.

Under the term of thermochemical pretreatment, any pretreatment that is known to one skilled in the art using alkaline and/or acid chemical agents and/or a heating of the biomass will be understood.

The pretreatment that is carried out in stage a) can be carried out according to numerous configurations that are known to one skilled in the art (Hendriks and Zeeman, Biores Technol, (2009) 100:10-18; Ogier et al., Oil & Gas Sci and Technol, (1999) 54: 67-94). It is possible to cite the Kraft-type pretreatment with sodium sulfate, a pretreatment by explosion of fibers with ammonia, also called AFEX (Ammonia Fiber Explosion) pretreatment or a pretreatment by percolation using ammonia with recycling, also called ARP (Ammonia Recycle Percolation) pretreatment. It is also possible to cite the acid baking or vapor explosion under acidic conditions.

The role of pretreatment is to make the cellulose accessible to enzymes by destructuring the lignocellulosic matrix. Based on the pretreatment that is implemented, preferably the lignin, the hemicelluloses or both at once is/are attacked.

Additional stages for setting the pH or liquefaction can be implemented so as to facilitate the use and the effectiveness of the process and in particular the course of the stages of enzymatic hydrolysis and ethylic fermentation.

The conversion of the cellulose into ethanol comprises at least one stage for enzymatic hydrolysis of cellulose into glucose and a stage for fermentation of glucose into ethanol, with these two stages being able to be produced separately or simultaneously. When the two stages are performed simultaneously, the process is called "SSF process."

The cellulolytic and/or hemicellulolytic enzymes that are used during the hydrolysis stage are produced by a microorganism that belongs to the genera *Trichoderma, Aspergillus, Penicillium* or *Schizophyllum*, or an anaerobic bacteria that belongs to the genus *Clostridium*.

Hydrolysis is preferably carried out at a pH of between 4 and 5.5 and at a temperature of between 40° C. and 60° C.

The ethylic fermentation implemented in stage d) is ensured by yeasts or other alcohologenic microorganisms.

The alcohologenic microorganisms used during the ethylic fermentation stage of the hexoses are preferably selected from among the yeasts and the bacteria, optionally genetically modified.

When the alcohologenic microorganism is a yeast, *Saccharomyces cerevisiae* is that which is the highest-performing. It is also possible to select yeasts such as *Schizosaccharomyces pombe* or *Saccharomyces uvarum* or *diastaticus*. More thermophilic yeasts, such as *Kluyveromyces fragilis* (now often referred to as *K. marxianus*), also have an advantage, in particular when enzymatic hydrolysis and ethylic fermentation are implemented simultaneously (SSF process).

A genetically modified organism, such as, for example, a yeast of the *Saccharomyces cerevisiae* type such as TMB 3400 (Ohgren et al, J. of Biotech 126, 488-498, 2006) can also be used. This yeast makes it possible to ferment into ethanol a portion of pentoses during the ethylic fermentation stage of hexoses, when the glucose is in a limiting concentration.

When the alcohologenic microorganism is a bacterium, *Zymomonas mobilis*, which has an effective assimilation path, will be preferred.

The ethylic fermentation is implemented preferably at a temperature that is between 30° C. and 40° C., and a pH of between 3 and 6.5.

The yeasts, and preferably *Saccharomyces cerevisiae*, are the microorganisms that are used in a very preferred way. They have a better robustness, and safety, and they do not require sterility for the performance of the process and installations.

The yeasts of the genus *Saccharomyces* are capable of fermenting the one and only hexoses (glucose and mannose essentially). These yeasts upgrade in an optimal way the hexoses into ethanol and make it possible to attain conversion yields on the order of 0.46 (p/p) to 0.48 (p/p), which is close to the maximum theoretical yield that amounts to 0.51 (p/p). Only the pentoses and several marginal carbon-containing sources are not used by these yeasts.

When enzymatic hydrolysis and ethylic fermentation are implemented in the same operation (SSF), the temperature is between 30 and 45° C., and the pH is between 4 and 6.

During stage e1), the alcohols and/or solvents produced in stage d) or present in stage d) after a recycling of the butyl wine are purified and separated. They are then separated by any method that is known to one skilled in the art, and in particular by distillation.

During stage e2), a solid cake that contains the insoluble residue is separated from vinasses containing sugars that are not fermented by the alcohologenic microorganism. The vinasses therefore contain non-fermented pentoses.

Stage e2) can be implemented downstream from stages c) and/or d) and can optionally be coupled to a washing cycle of the cake. The washing makes it possible to improve the recovery of sugars obtained from hydrolysis (stage c), alcohols and/or solvents produced during stage d) or present because of recycling, and/or also sugars that are not fermented by the microorganism during stage d).

During the fermentation stage f) by a solventogenic microorganism, the sugars of the vinasses and in particular the non-fermented pentoses are converted into a butyl wine, for example an ABE (acetone-butanol-ethanol) mixture or an IBE (isopropanol-butanol-ethanol) mixture by microorganism strains. The mixture of solvents that are obtained depends on the microorganism that is used for the fermentation.

The solventogenic microorganisms that are used during the butylic fermentation stage are selected from among the wild strains belonging to the genus *Clostridium* or genetically modified strains belonging to the species *Escherichia coli*.

In a preferred way, the solventogenic microorganism is a bacterium of the genus *Clostridium*, a strictly anaerobic microorganism that is capable of metabolizing the pentoses into butyl wine, in the presence or absence of hexoses.

For example, *Clostridium beijerinckii, Clostridium saccharobutylicum, Clostridium saccharoperbutylacetonicum* and *Clostridium acetobutylicum* produce an acetone/butanol/ethanol mixture or an ABE mixture in proportions that are close to 30%/60%/10%.

*Clostridium*, a more difficult microorganism to cultivate than the yeast *Saccharomyces cerevisiae*, is used in a medium that has been partially detoxified by yeast [Ohgren et al., Appl Biochem Biotechnol (2005) 121-124: 1055-1067; Klinke et al., Appl Microbiol Biotechnol (2004) 66: 10-26], which reduces in particular the main aldehydes.

This is particularly advantageous in the case of lignocellulosic hydrolyzates obtained from acid-type pretreatments that result in the production of furanic compounds, phenolic compounds, and organic acids that are known for being toxic for the microorganisms.

According to one embodiment, the pentoses that are fermented during stage f) are contained in the vinasses.

In a preferred way, the vinasses, which are sent to stage f) for butylic fermentation, have a sugar concentration of between 30 and 90 g/L of sugars or fermentable products.

If the concentration of sugars or fermentable products is not adequate, a particular embodiment makes it possible to deflect this stream downstream from the pretreatment stage before sending it to the fermentation stage f). This makes it possible to put insoluble materials into suspension and to enrich pentoses and sugars that are not used by the ethylic fermentation.

Also according to another mode, the pentoses that are fermented in stage f) come from both vinasses and a stream that is directly extracted after the pretreatment stage.

Preferably, the concentration in butanol at the end of the butylic fermentation stage f) is between 1 and 20 g/L. For ABE or IBE mixtures, the total concentration of solvents is between 5 and 30 g/L.

According to the invention, at least a portion of the butyl wine is recycled downstream from the pretreatment stage a).

The inactivation of the solventogenic microorganism is carried out either by an increase in the temperature or by a modification of the pH, or any other technique that is known to one skilled in the art. The modification of the pH is preferred to the extent that a stage for setting the pH may be necessary for the enzymatic hydrolysis stage (stage b) after the pretreatment (stage a).

According to one embodiment, the stream containing butyl wine exiting from the butylic fermentation stage is divided into two streams, one being recycled downstream from the pretreatment stage.

The second stream can be sent to a stage for water/solvents separation, before being also recycled and sent to the reactor where stage e) takes place.

According to another embodiment, the second stream is used for other applications without recycling.

According to another embodiment, the entire stream containing the butyl wine exiting from the butylic fermentation stage is recycled downstream from the pretreatment stage. In this case, a portion of the vinasses obtained from stage e) is extracted without being sent to the fermentation stage f). The sugars that are contained in these vinasses can be upgraded in an independent way.

Once the recycling of a portion of the butyl wine is carried out, the aqueous stream entering into the reactor for conversion of the cellulose preferably contains between 0.1 and 20 g/L of solvents, including butanol, with a concentration of between 0.1 and 15 g/L.

The butyl and ethyl wines subjected to extraction (stage e) can contain between 0.1 and 20 g/L of solvents including 0.1 and 15 g/L of butanol, and between 10 and 150 g/L of ethanol produced by fermentation of hexoses. The concentration of ethanol depends, on the one hand, on the content of dry material, stages of enzymatic hydrolysis and fermentation, and, on the other hand, optional additions of sugar that it is possible to provide. It is possible to consider adding to the medium by sugar from sugar cane or sugar beets or amylase plants.

The invention will be described in a detailed way by referring to the figures.

The substrate is introduced via the pipe 1 into the pretreatment reactor (2). The reagents and utilities such as steam that are necessary for properly conducting the pretreatment are introduced via the piping 3, and the residues (condensates, black liquor, washing waters, . . . ) that are extracted are introduced via the pipe 4. Recycling, reuse or treatment of this stream is inherent to each type of pretreatment and is not presented in detail here.

The pretreated substrate is extracted via the pipe 6. It preferably contains between 5% (p/v) and 60% (p/v) of MS, more preferably between 15% (p/v) and 60% (p/v) of MS, and even more preferably between 30% (p/v) and 60% (p/v) of MS.

Thus, according to the embodiment that is shown in FIG. 1, the pretreated substrate that is extracted via the pipe 6 contains the majority of pentoses, in solid form (pentosans) or in soluble form.

According to a variant of the process (not in accordance with the invention), a stream 5 that contains pentoses for the most part is extracted directly during the pretreatment and is sent to the reactor 14 in which the butylic fermentation takes place.

According to another variant, not shown, the pentoses can be extracted in part in the stream 5 and in part in the pretreated substrate that circulates in the pipe 6, and with these two streams mixed entirely or in part before the butylic fermentation.

The reactor 7 is the reactor in which the conversion of cellulose into ethanol is carried out.

The conditions of enzymatic hydrolysis, primarily the level of dry material of the mixture to be hydrolyzed and the amount of enzymes used, are selected in such a way that stage c) is carried out to be able to obtain a solubilization of the cellulose of between 20% and 99% within the reactor 7, and more particularly between 30% and 95%. The water that is necessary for obtaining the targeted level of MS is added via the pipe 8. The desired level of MS is between 5% (p/v) and 45% (p/v) and preferably between 8% (p/v) and 35% (p/v).

The cellulolytic and/or hemicellulolytic enzymes are added via the piping 8a.

The alcohologenic microorganisms that are used for ethylic fermentation are introduced via the piping 8b and can also be produced in situ starting from the glucose that is present.

The additives that are necessary for setting the pH or liquefaction are introduced via the piping 8c.

The extraction of the alcohols and/or solvents produced during the ethylic fermentation stage is carried out in the reactor 11. The alcohol and/or the solvents are preferably extracted by distillation, via the pipe 12.

The cake containing the insoluble residue is extracted via the piping (9a) and/or (9b).

In the reactor 11a, the separation of the ethanol and/or solvents is performed, and vinasses are extracted via the piping 13.

In the reactor 11b, the separation between the ethanol and/or the solvents and the water for extracting a stream of products is carried out more specifically via the piping 12.

Thus, at the outlet of stages c) to e) carried out in the reactors 7 and 11, a stream of products 12 (alcohol and/or solvents) extracted by any means known to one skilled in the art is obtained, with a liquid residue 13 (called vinasses) containing non-fermented sugars with, in particular, pentoses (xylose, arabinose), and even traces of hexoses (galactose, for example, with hexose the most difficult to metabolize by the conventional yeasts) as well as oligomers and a solid cake 9 containing the solid material that is obtained from the initial substrate (solid residue) and a liquid fraction, because of the limitations of the solid/liquid separation equipment. The solid residue is in part composed of cellulose and hemicellulose that has not been hydrolyzed and lignin.

The solventogenic microorganism that is used during the butylic fermentation stage of the pentoses, preferably *Clostridium*, is introduced into the reactor 14 via the pipe 15a to be mixed with the vinasse 13. The utilities and additives that are necessary for properly conducting the fermentation are introduced via the pipe 15b. The reactor 14 can be a sterilizable reactor. The fermentation gases are evacuated. The pH in this reactor can be monitored and regulated if necessary.

The stream exiting from the reactor 14 via the piping 16 corresponds to the butyl wine. It is not useful to separate the microorganisms.

The aqueous stream entering into the reactor for hydrolysis and/or fermentation of hexoses contains between 1 and 20 g/L of solvents, with the concentration of butanol being between 0.1 and 15 g/L.

The wines that are obtained are subjected to extraction in the reactor 11 (stage e).

According to the embodiment shown in FIG. 1, the stream 16 exiting from the butylic fermentation stage is divided into two streams. The stream 16a is recycled downstream from the pretreatment stage.

The stream 16b can be sent to a water/solvent separation stage in a reactor 17, before being also recycled and returned to the separation reactor 11 via a pipe 18.

According to another embodiment, the stream 16b is used for other applications without recycling.

Figure 2:
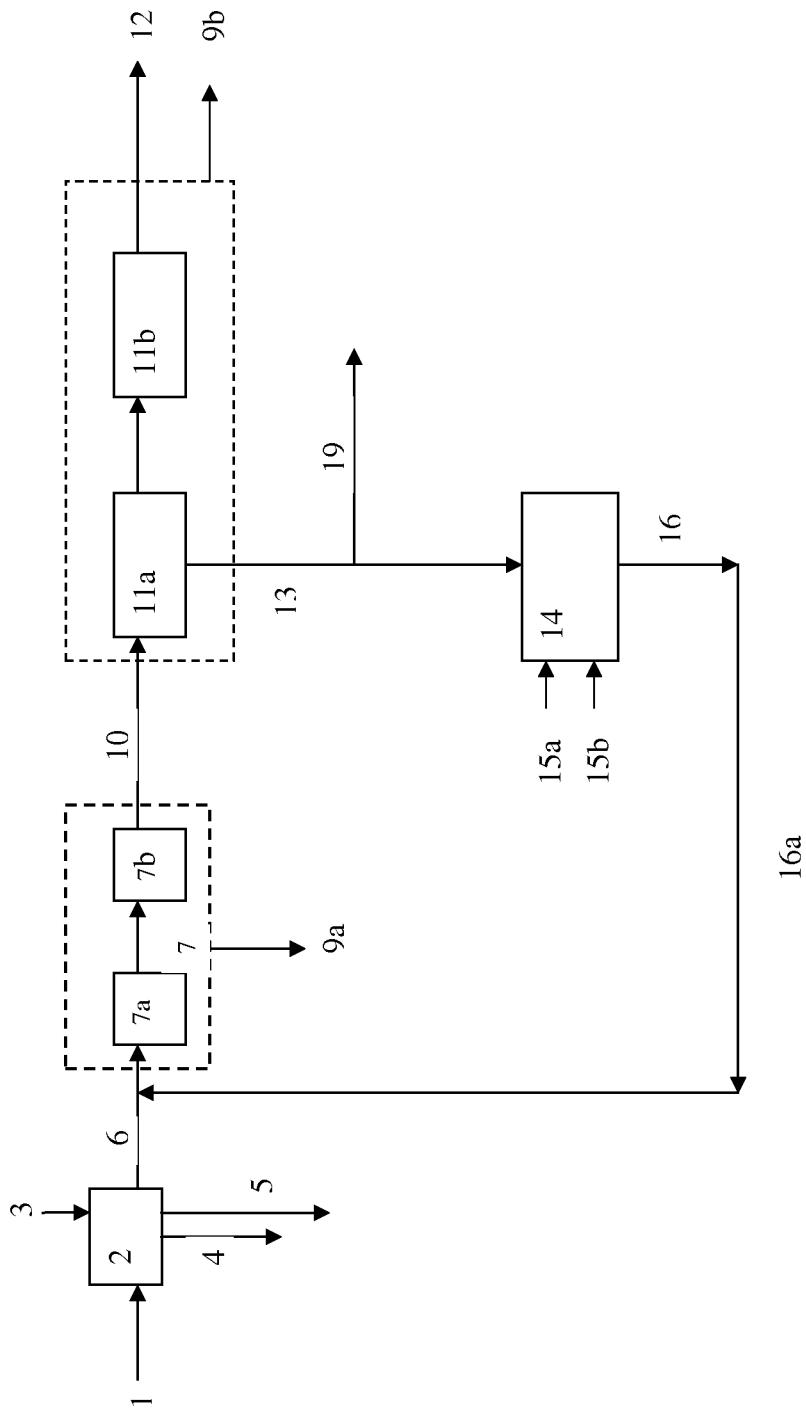
FIG. 2 is a diagrammatic representation of a process for the production of alcohols and/or solvents starting from lignocellulosic substrates, comprising a stage for recycling butyl wine, according to a second embodiment.

According to the embodiment that is shown in FIG. 2, the entire stream 16 that exits from the butylic fermentation reactor is recycled downstream from the pretreatment stage. The portion of excess vinasses that is not sent to the fermentation stage f) is extracted via the piping 19. The sugars that are contained in these vinasses can be upgraded in an independent way.

Owing to the process according to the invention, the savings realized in the single extraction stage is substantial. As shown in the following examples, it can reach up to 40%.

EXAMPLES

The examples below illustrate the invention without limiting its scope.

Example 1

Not in Accordance with the Invention

A process for the production of ethanol, butanol and acetone starting from "Kraft"-type papermaking paste is considered. The paste is obtained starting from "softwood" wood that is pretreated in a Kraft-type papermaking process, which is an alkaline process in the presence of soda. The lignin-poor paste that is obtained from Kraft is then washed and neutralized and then introduced into the process for conversion of cellulosic substrate into ethanol by enzymatic hydrolysis and fermentation of glucose and mannose (sugars with 6 carbon atoms).

The process treats 52 tons/hour of paste (dry material base). The composition of the dry material is as follows:

| | |
|---|---|
| Cellulose (%) | 40% |
| Xylans (%) | 7.5% |
| Mannans (%) | 7.5% |
| Lignin (%) | 33% |
| Others (%) | 12% |

During pretreatment, the losses of cellulose and hemicellulose are on the order respectively of 1.5 and 50.7%. At the outlet of the pretreatment, the level of dry material is 59%.

The process for conversion into ethanol, butanol and acetone contains the following stages: enzymatic hydrolysis, ethylic fermentation of hexoses, separation of solid residues of wines, distillation and dehydration of ethanol, fermentation of the vinasse fraction into ABE (acetone, butanol and ethanol), and distillation and separation of the acetone and ethanol fractions from the butanol fraction.

Eyzymatic hydrolysis is performed at pH 5, with an inlet stream containing 20% (p/v) of material in suspension. Under the selected hydrolysis conditions, 70% of the polymers of sugars are solubilized into monomers.

The sugary juice is then sent to ethylic fermentation where 90% of the glucose and mannose sugars are converted into ethanol.

The wine is sent to a centrifuging device for separating the solid and liquid phases.

The liquid phase is then sent into distillation. For the most part, the top product contains the fractions of ethanol and/or solvents that are present (ethanol and optionally acetone, and butanol in the case of a scheme with recycling); the bottom product contains vinasses (water mixture, pentoses, and the solids that are still present).

The vinasses are sent to the ABE fermentation stage. The pentoses are respectively converted into butanol, ethanol, acetone and acid by-products for, respectively, 56.7, 4.55, 36.1 and 2.75% (molar).

In the absence of recycling, the ethanol fraction that is recovered at the top of the distillation is sent to a rectification column, yielding an ethanol-water mixture in azeotrope.

The products that are obtained from the ABE fermentation are sent to two distillation columns that will separate the water and then the ethanol, acetone and butanol fractions.

For this process scheme, production of ethanol, acetone and butanol is respectively 7.4, 0.12 and 0.24 t/h.

The overall energy consumption of the process is 21.4 MW, which corresponds to a mean consumption of 10 MJ/kg of solvent that is produced.

Example 2

In Accordance with the Invention

The process is identical to the one of Example 1 but describes a recycling of the stream obtained after the butylic fermentation stage at two points:

The first recycling, corresponding to 85.7% of this stream, is sent upstream from enzymatic hydrolysis; the remainder is sent to the ABE common separation after separation of the wines. The addition of additional water is zero at the level of enzymatic hydrolysis.

The fraction of the alcohols and/or solvents recovered at the top of the wine distillation column is sent to two distillation columns for separating the ethanol, acetone and butanol fractions.

For this process scheme, production of ethanol, acetone and butanol is respectively 7.5, 0.11 and 0.24 t/h.

The overall energy consumption of the process is 15.7 MW, which corresponds to a mean consumption of 7.2 MJ/kg of solvent that is produced.

For this version with two recycling processes, the scheme with ABE recycling makes possible an increase in energy that may reach 28% (MJ/kg of solvent).

Example 3

In Accordance with the Invention

The process is identical to the one of Example 2 in which only a portion of the stream—that is obtained after the butylic fermentation stage is recycled upstream from enzymatic hydrolysis—is recycled. The portion of the non-recycled stream is used for other applications.

The recycling, corresponding to 85.7% of this stream, is sent upstream from enzymatic hydrolysis. The addition of additional water is zero at the level of enzymatic hydrolysis.

The fraction of alcohols and/or solvents recovered at the top of the wind distillation column is sent to two distribution columns for separating the ethanol, acetone and butanol fractions.

For this process scheme, production of ethanol, acetone and butanol is respectively 7.4, 0.10 and 0.2 t/h.

The overall energy consumption of the process is 13.6 MW, which corresponds to a mean consumption of 6.3 MJ/kg of solvent that is produced.

In this configuration, the number of pieces of equipment required by the process is reduced by one distillation column.

For this version with a single recycling and a purging, the scheme with ABE recycling makes possible an increase in equipment and an increase in energy that can reach 37% (MJ/kg of solvent).

Example 4

Not in Accordance with the Invention

The same process for production of ethanol, butanol and acetone as the one that is described in Example 1, but with a different substrate and pretreatment, is considered.

The substrate that is used is straw, pretreated under acid conditions. The paste is then washed and neutralized, and then introduced into the process for conversion of cellulosic substrate into ethanol by enzymatic hydrolysis and fermentation of glucose and mannose (sugars with 6 carbon atoms).

The process treats 52 tons/hour of paste (dry material base). The composition of the dry material is as follows:

| | |
|---|---|
| Cellulose (%) | 41.7% |
| Xylans (%) | 25.2% |
| Mannans (%) | 0% |
| Lignin (%) | 23.2% |
| Others (%) | 9.9% |

During pretreatment, the losses of cellulose and hemicelluloses are on the order respectively of 5 and 10%. At the outlet of the pretreatment, the level of dry material is 35% (p/v).

The process for conversion into ethanol, butanol and acetone contains the following stages: enzymatic hydrolysis, ethylic fermentation of hexoses, separation of the solid residues of wines, distillation and dehydration of ethanol, fermentation of the vinasse fraction into ABE (acetone, butanol and ethanol), and distillation and separation of the acetone and ethanol fractions from the butanol fraction.

Enzymatic hydrolysis is performed at pH 5, with an inlet stream containing 11.8% of material in suspension. Under the selected hydrolysis conditions, 95% of the polymers of sugars are solubilized into monomers.

The sugary juice is then sent into ethylic fermentation where 90% of the glucose and mannose sugars are converted into ethanol.

The wine is sent to a centrifuging device for separating the solid and liquid phases.

The liquid phase is next sent into distillation. The top product for the most part contains the solvent fractions that are present (ethanol and optionally acetone and butanol in the case of a scheme with recycling); the bottom product contains vinasses (water mixture, sugars with 5 carbon atoms and the solids that are still present).

The vinasses are sent to the ABE fermentation stage. The pentoses are respectively converted into butanol, ethanol, acetone and acid by-products for respectively 56.7, 4.55, 36.1 and 2.75% (molar).

In the absence of recycling, the ethanol fraction that is recovered at the top of the distillation is sent to a rectification column, yielding an ethanol-water mixture in azeotrope.

The products that are obtained from the ABE fermentation are sent to two distillation columns that will separate the water and then the ethanol, acetone and butanol fractions. For this process scheme, production of ethanol, acetone and butanol is respectively 9.8, 1.27 and 2.91 t/h.

The overall energy consumption of the process is 41.7 MW, which corresponds to a mean consumption of 10.8 MJ/kg of solvent produced.

Example 5

In Accordance with the Invention

The same process for production of ethanol, butanol and acetone as the one that is described in Example 2, but with a different substrate and pretreatment, is considered.

The ABE post-fermentation stream is recycled at two points. The first recycling, corresponding to 65.7% of this stream, is sent upstream from enzymatic hydrolysis; the remainder is sent to the ABE common separation after separation of the wines. The addition of additional water is zero at the level of enzymatic hydrolysis.

The fraction of alcohols and/or solvents recovered at the top of the distillation column of the wines is sent to two distillation columns for separating the ethanol, acetone and butanol fractions.

For this process scheme, production of ethanol, acetone and butanol is respectively 9.8, 1.21 and 2.85 t/h.

The overall energy consumption of the process is 33.8 MW, which corresponds to an overall mean consumption of 8.8 MJ/kg of solvent that is produced.

For this version with two recycling steps, the scheme with ABE recycling makes possible an increase in energy that can reach 18% (MJ/kg of solvent).

Example 6

In Accordance with the Invention

The same process for production of ethanol, butanol and acetone as the one described in Example 3, but with a different substrate and pretreatment, is considered.

The recycling, corresponding to 65.7% of this stream, is sent upstream from enzymatic hydrolysis. The addition of additional water is zero at the level of enzymatic hydrolysis.

The fraction of alcohols and/or solvents recovered at the top of the wine distillation column is sent to two distillation columns for separating the ethanol, acetone and butanol fractions.

For this process scheme, production of ethanol, acetone and butanol is respectively 9.7, 0.8 and 1.9 t/h.

The overall energy consumption of the process is 32.3 MW, which corresponds to an overall mean consumption of 9.3 MJ/kg of solvent that is produced.

In this configuration, the number of pieces of equipment required by the process is reduced by one distillation column.

For this version with a single recycling and a purging, the scheme with ABE recycling makes possible an increase in equipment and an increase in energy up to 13% (MJ/kg of solvent).

The invention claimed is:

1. A process for the production of alcohols, solvents, or both starting from cellulosic or lignocellulosic biomass comprising the following steps:

a) pretreating a cellulosic or lignocellulosic substrate by thermochemical pretreatment to produce a pretreated substrate;
b) optionally washing said pretreated substrate and adjusting the pH of said pretreated substrate;
c) hydrolyzing said pretreated, optionally washed, substrate, with cellulolytic and/or hemicellulolytic enzymes, wherein an aqueous stream comprising a hydrolysate and a water-insoluble residue is produced;
d) fermenting hexoses contained in said hydrolysate obtained from step c) in the presence of an alcohologenic microorganism of the genus *Saccharomyces* to produce an ethyl wine comprising ethanol and solvents;
e) extracting said ethyl wine of step d), said extracting comprising
   e1) separating and purifying ethanol and/or solvents obtained from step d), and
   e2) separating a solid cake containing said water-insoluble residue to produce vinasses;
f) fermenting pentoses contained in said vinasses obtained from step e2) in the presence of a solventogenic microorganism of the genus *Clostridium* to produce a butyl wine, wherein said butyl wine comprises a mixture of solvents comprising acetone, butanol, and ethanol, or comprises a mixture of solvents comprising isopropanol, butanol, and ethanol;
g) recycling at least a portion of said butyl wine upstream from at least one of step c) and/or step d), wherein after said recycling of at least a portion of said butyl wine said aqueous stream in step c) contains between 0.1 and 20 g/L of solvents, and a butanol portion of said solvents is present in a concentration of between 0.1 and 15 g/L.

2. The process of claim 1, wherein said pentoses fermented in step f) are obtained both from said vinasses from step e2) and a stream that is extracted directly after step a).

3. The process of claim 1, wherein steps c) and d) are carried out simultaneously at a temperature range of 30° to 45° C., and at a pH range of 4 to 6.

4. The process of claim 1, wherein said separating said solid cake of step e2) is carried out downstream from step c) and/or step d) and is optionally coupled to a washing cycle of said solid cake.

5. The process of claim 1, wherein said vinasses sent to said fermenting in step f) have a concentration range of 30 to 90 g/L of sugars or fermentable products.

6. The process of claim 1, wherein said vinasses are sent downstream from said pretreating in step a) before being sent to said fermenting in step f).

7. The process of claim 1, wherein a portion of said butyl wine that is not recycled upstream from at least one of step c) and/or step d) is subjected to a water/solvent separation before being sent to said extracting step e).

8. The process of claim 7, wherein said ethyl and butyl wines subjected to said extracting step e) contain 10 to 150 g/L of ethanol and 0.1 to 20 g/L of solvents, wherein said solvents comprise 0.1 to 15 g/L of butanol.

* * * * *